United States Patent
Na et al.

(10) Patent No.: US 10,196,682 B2
(45) Date of Patent: Feb. 5, 2019

(54) SENSOR FOR DETECTION OF ZINC OXIDE NANOWIRES AND METHOD FOR DETECTION OF ZINC OXIDE NANOWIRES IN WATER USING THE SENSOR

(71) Applicant: KOREA UNIVERSITY RESEARCH AND BUSINESS FOUNDATION, Seoul (KR)

(72) Inventors: Sung Soo Na, Seoul (KR); Jinsung Park, Seoul (KR); June Seok You, Busan (KR); Kyu Whan Jang, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 69 days.

(21) Appl. No.: 15/253,122

(22) Filed: Aug. 31, 2016

(65) Prior Publication Data

US 2017/0058333 A1  Mar. 2, 2017

(30) Foreign Application Priority Data

Sep. 1, 2015 (KR) .................. 10-2015-0123664

(51) Int. Cl.
*C12Q 1/6834* (2018.01)
*C12Q 1/6816* (2018.01)
*B82Y 15/00* (2011.01)

(52) U.S. Cl.
CPC ......... *C12Q 1/6834* (2013.01); *C12Q 1/6816* (2013.01); *B82Y 15/00* (2013.01)

(58) Field of Classification Search
CPC ..... C12Q 1/6816; C12Q 1/6834; B82Y 15/00
See application file for complete search history.

(56) References Cited

U.S. PATENT DOCUMENTS

2013/0260113 A1* 10/2013 Hart .................. B32B 3/22
428/201

OTHER PUBLICATIONS

Chen et al, Zinc oxide nanoparticle decorated multi-walled carbon nanotubes and their optical properties, 2006, Acta Materialia, 54, 5401-5407. (Year: 2006).*
Jang et al, Highly sensitive detection of self-aggregated single-walled carbon nanotubes using a DNA-immobilized resonator, 2013, Chem. Commun., 49, 8635-8637. (Year: 2013).*
You et al, Label-free detection of zinc oxide nanowire using a graphene wrapping method, 2015, Biosensors and Bioelectronics, 68, 481-486, publicly available on Jan. 19, 2015. (Year: 2015).*

* cited by examiner

*Primary Examiner* — Narayan K Bhat
(74) *Attorney, Agent, or Firm* — Oblon, McClelland, Maier & Neustadt, L.L.P.

(57) ABSTRACT

Disclosed are a sensor capable of detecting zinc oxide nanowires in water with high selectivity and sensitivity and a method for the detection of zinc oxide nanowires in water using the sensor. The sensor and method can provide powerful tools for analyzing the toxicity of zinc oxide nanowires to the environment and humans due to their ability to detect zinc oxide nanowires in water with high selectivity and sensitivity.

12 Claims, 5 Drawing Sheets

Specification includes a Sequence Listing.

SEQUENCE LISTING

<160> NUMBER OF SEQ ID NOS: 1

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
tttttttttt tttttttttt tttttttttt                                          30

SENSOR FOR DETECTION OF ZINC OXIDE NANOWIRES AND METHOD FOR DETECTION OF ZINC OXIDE NANOWIRES IN WATER USING THE SENSOR

BACKGROUND OF THE INVENTION

1. Field of the Invention

The present invention relates to a sensor capable of detecting zinc oxide nanowires in water with high selectivity and sensitivity and a method for the detection of zinc oxide nanowires in water using the sensor.

2. Description of the Related Art

Nanomaterials have recently attracted a considerable attention due to their physical, chemical, optical, and electrical properties different from the typical properties of their bulk phase (Moezzi et al., 2012). Thus, the use of such nanomaterials has grown rapidly for commercial purposes as well as research purposes. Various commercial products, including sunscreens, tennis rackets, solid lubricants, and detergents, use nanomaterials to enhance their performance. Among various types of nanomaterials, zinc oxide nanowires (ZnONWs) have received great interest due to their unique piezoelectric and semiconducting properties (Chen et al., 2011; Hempen and Karst, 2006; Huang et al., 2006; Nasr et al., 2013; Riaz et al., 2011; Wang et al., 2008; Williams and Kamat, 2009) and have been explored for various applications, including piezoelectric devices, energy harvesting devices, self-powered nanosensors, and biomedical devices (Agrawal and Espinosa, 2011; Lin et al., 2012; Rasmussen et al., 2010; Wang and Song, 2006).

The toxicity of zinc oxide nanowires to humans and the environment needs to be analyzed before their use in industrial and commercial products. Thus, studies on the toxicity of zinc oxide have recently been reported (Nel et al., 2006). Since zinc oxide was declared as a toxic substance by the Organization for Economic Cooperation and Development (OECD), its potential toxicity has been a concern.

Specifically, as the size of zinc oxide nanowires decreases to the nanometer scale, the surface area per unit volume increases extensively and chemical reactions occur to cause rapid production of reactive oxygen species (ROS) in organisms (George et al., 2009). Eventually, the rapid production of ROS causes damage to mitochondria, cell membrane, and nuclear DNA, leading to the malfunction of enzymes or the death of cells (Ryter et al., 2007). Further, when zinc oxide nanowires enter cells, a degradation process occurs to generate zinc ions ($Zn^{2+}$) due to the weakly acidic environment. The zinc ions tend to cause toxic phenomena, which are potentially harmful to the cells. The critical concentration of zinc oxide nanowires for human monocyte macrophages was reported to be 10 μg/mL or less in a weakly acidic solution (Müller et al., 2010). Generally, a concentration of 25 μg/mL of zinc oxide is considered as the effective toxicity in neutral solutions (George et al., 2009; Xia et al., 2008).

As applications based on zinc oxide nanowires develop, human exposure to zinc oxide nanowires increases, which is considered as a potential hazard to human health. Due to their very small size, an increased amount of zinc oxide nanowires will be discharged in the form of industrial waste to the water system. When exposed to the environment, zinc oxide nanowires would be accumulated in the human body along the food chain, which will adversely affect human health later on. Thus, there is an increasing need to monitor the concentration of zinc oxide nanowires.

Numerous approaches to the detection of toxic nanomaterials in water have been proposed, for example, by atomic absorption spectroscopy (M. Ghaedi, F. Ahmadi and A. Shokrollahi, J. Hazard. Mater., 2007, 142, 272-278), fluorometry based optical methods (Y. Wen, F. Xing, S. He, S. Song, L. Wang, Y. Long, D. Li and C. Fan, Chem. Commun., 2010, 46, 2596-2598), surface plasmon resonance (T. Kang, S. Hong, J. Moon, S. Oh and J. Yi, Chem. Commun., 2005, 3721-3723), surface-enhanced Raman scattering (J. Yin, T. Wu, J. Song, Q. Zhang, S. Liu, R. Xu and H. Duan, Chem. Mater., 2011, 23, 4756-4764), electrochemical methods (Z. Lin, X. Li and H. B. Kraatz, Anal. Chem., 2011, 83, 6896-6901), and methods using resonators (J. Park, W. Choi, K. Jang and S. Na, Biosens. Bioelectron., 2013, 41, 471-476). These approaches are useful for selective detection of many nanomaterials but, to our knowledge, no successful methods for selective detection of zinc oxide nanowires in water have been reported to date.

SUMMARY OF THE INVENTION

The present invention has been made in view of the above problems, and it is an object of the present invention to provide a sensor capable of detecting zinc oxide nanowires with high selectivity and sensitivity and a method for the detection of zinc oxide nanowires in water using the sensor.

One aspect of the present invention provides a sensor for the detection of zinc oxide nanowires in water, including a carbon material binding with zinc oxide nanowires in water, single-stranded DNA (ssDNA) capable of selective binding to the carbon material, and a microresonator surface immobilized with the single-stranded DNA wherein the mass of the microresonator is increased by the binding of the carbon material with the single-stranded DNA to cause the shift of the resonance frequency.

According to one embodiment of the present invention, the carbon material may be selected from the group consisting of reduced graphene oxide, graphene oxide, carbon nanotubes, and mixtures thereof.

According to a further embodiment of the present invention, the single-stranded DNA may include a plurality of thymine bases. In this embodiment, the single-stranded DNA may be 5'-$(TTT)_n$-3' ($1 \leq n \leq 20$).

Another aspect of the present invention provides a method for the detection of zinc oxide nanowires in water, including (a) preparing a liquid sample including zinc oxide nanowires and adding a carbon material binding with the zinc oxide nanowires to the liquid sample to coat the surface of the zinc oxide nanowires with the carbon material, (b) immobilizing single-stranded DNA (ssDNA) capable of selective binding to the carbon material on the surface of a microresonator, (c) immersing the surface of the microresonator in the liquid sample to induce selective binding between the carbon material and the single-stranded DNA, and (d) analyzing the resonance frequency shift of the microresonator caused by a mass increase of the microresonator due to the selective binding.

According to one embodiment of the present invention, the carbon material may be selected from the group consisting of reduced graphene oxide, graphene oxide, carbon nanotubes, and mixtures thereof.

According to a further embodiment of the present invention, the single-stranded DNA may include a plurality of thymine bases. In this embodiment, the single-stranded DNA may be 5'-$(TTT)_n$-3' ($1 \leq n \leq 20$).

According to another embodiment of the present invention, the resonance frequency shift can be given by:

$$\omega_{nrfs} = \delta_\omega \times 100/\omega_0$$

where $\omega_0$ is the resonance frequency measured after immobilization of the single-stranded DNA on the surface of the microresonator and $\delta_\omega$ is the resonance frequency measured after selective binding between the carbon material and the single-stranded DNA.

According to the present invention, zinc oxide nanowires in water can be detected with high selectivity and sensitivity. Therefore, the present invention provides powerful tools for analyzing the toxicity of zinc oxide nanowires to the environment and humans.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

The present invention will now be described in more detail.

The present invention is directed to a sensor capable of detecting zinc oxide nanowires in water with high selectivity and sensitivity and a novel method for the detection of zinc oxide nanowires in water using the sensor.

Figure 1:
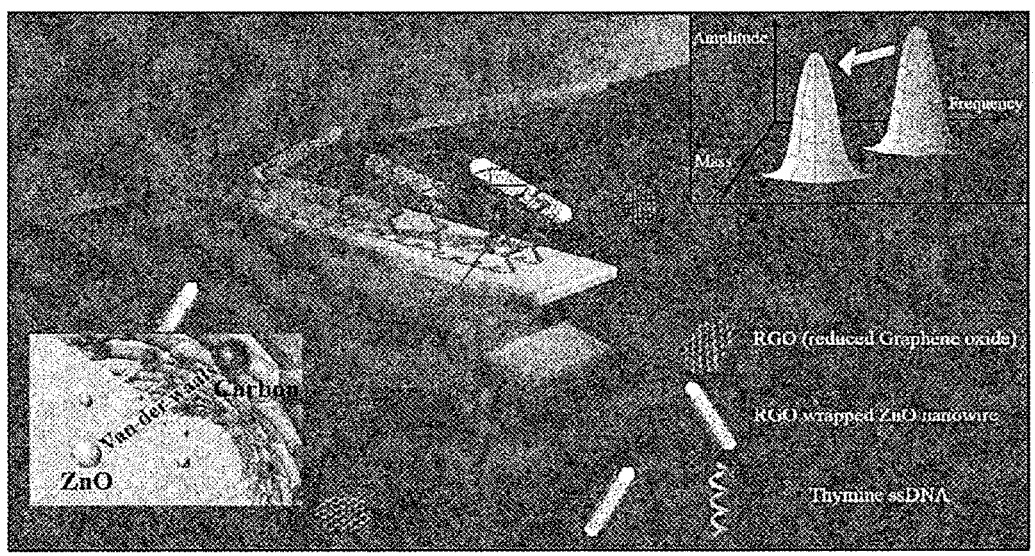
FIG. 1 is a schematic conceptual diagram showing the structure of a sensor according to the present invention and the detection of zinc oxide nanowires in water using the sensor based on the resonance frequency shift arisen from the interaction between single-stranded DNA (ssDNA) immobilized on the surface of a microresonator and reduced graphene oxide bound with zinc oxide nanowires (RGO-ZnONWs)

FIG. 1 is a schematic conceptual diagram showing the structure of a sensor according to the present invention and the detection of zinc oxide nanowires in water using the sensor. The detection is based on the resonance frequency shift arisen from the interaction between single-stranded DNA (ssDNA) immobilized on the surface of a microresonator and reduced graphene oxide bound with zinc oxide nanowires (RGO-ZnONWs). The sensor shown in FIG. 1 can detect zinc oxide nanowires in water with high selectivity and sensitivity using the self-aggregation mechanism between zinc oxide nanowires (ZnONWs) and reduced graphene oxide resulting from the strong Van der Waals attractive forces between the zinc atoms (Zn) of the zinc oxide nanowires and the carbon atoms (C) of the reduced graphene oxide (RGO) and the resonance frequency shift of a microresonator caused by the strong interaction between single-stranded DNA (ssDNA) and the reduced graphene oxide.

Specifically, the sensor of the present invention includes a carbon material binding with zinc oxide nanowires in water, single-stranded DNA (ssDNA) capable of selective binding to the carbon material, and a microresonator surface immobilized with the single-stranded DNA wherein the mass of the microresonator is increased by the binding of the carbon material with the single-stranded DNA to cause the shift of the resonance frequency.

The carbon material may be any material that includes carbon atoms capable of binding with the zinc atoms of the zinc oxide nanowires and can bind with the single-stranded DNA immobilized on the microresonator by the π-π interaction. The carbon material may be selected from the group consisting of, but not limited to, reduced graphene oxide, graphene oxide, carbon nanotubes, and mixtures thereof. Reduced graphene oxide is more preferred as the carbon material, as can be seen from the results in the Examples section that follows.

The single-stranded DNA is required to have the ability to bind to the carbon material bound with the zinc oxide nanowires by the π-πinteraction. It is thus preferred that the single-stranded DNA includes a plurality of thymine bases. The single-stranded DNA can be expressed by 5'-(TTT)$_n$-3' (1≤n≤20). A specific example of the single-stranded DNA may be 5'-TTT TTT TTT TTT TTT TTT TTT TTT TTT-3' (SEQ ID NO: 1).

The present invention also provides a method for the detection of zinc oxide nanowires in water, including (a) preparing a liquid sample including zinc oxide nanowires and adding a carbon material binding with the zinc oxide nanowires to the liquid sample to coat the surface of the zinc oxide nanowires with the carbon material, (b) immobilizing single-stranded DNA (ssDNA) capable of selective binding to the carbon material on the surface of a microresonator, (c) immersing the surface of the microresonator in the liquid sample to induce selective binding between the carbon material and the single-stranded DNA, and (d) analyzing the resonance frequency shift of the microresonator caused by a mass increase of the microresonator due to the selective binding.

The carbon material and the single-stranded DNA are the same as those described above. The resonance frequency shift, $\omega_{nrfs}$, caused by selective binding between the carbon material bound with zinc oxide nanowires and the single-stranded DNA (ssDNA) immobilized on the surface of the microresonator can be given by:

$$\omega_{nrfs} = \delta\omega \times 100/\omega_0$$

where $\omega_0$ is the resonance frequency measured after immobilization of the single-stranded DNA on the surface of the microresonator and $\delta_\omega$ is the resonance frequency measured after selective binding between the carbon material and the single-stranded DNA.

The present invention will be described in more detail with reference to the following examples. It will be obvious to those skilled in the art that these examples are provided for illustrative purposes and the scope of the invention is not limited thereto.

1. Materials and Method 1-1. Materials

The following materials were purchased from Sigma-Aldrich (St. Louis, MO, USA): sodium dodecyl sulfate (SDS), sodium carbonate ($Na_2CO_3$), zinc chloride ($ZnCl_2$), silicon monoxide (SiO), sulfuric acid ($H_2SO_4$), hydrogen peroxide solution ($H_2O_2$), dimethyl sulfoxide (DMSO), and tris-ethylene diamine tetraacetic acid (EDTA) buffer solution. The 5'-TTT TTT TTT TTT TTT TTT TTT TTT TTT TTT-3' (SEQ ID NO: 1) DNA was purchased from Integrated DNA Technology (Coralville, Iowa, USA). Silver nanowires were purchased from Ditto Technology (Seoul, Korea) and reduced graphene oxide (RGO) was purchased from Nanocs (Boston, Mass., USA).

1-2. Synthesis of Zinc Oxide Nanowires (ZnONWs) and Silicon Dioxide Nanowires ($SiO_2$NWs)

For the synthesis of ZnONWs, 1.25 g of $ZnCl_2$, 5 g of SDS, and 25 g of $Na_2CO_3$ were added to 50 mL of deionized water. Then, the mixture was mixed using a magnetic stirrer for 30 min and kept at 400 K for 12 h. The mixture was filtered and dried to obtain ZnONWs powders. Similarly, $SiO_2$ nanowires were prepared using silicon monoxide powder (purity: 99.99%, particle size: 73 μm) (Hu et al., 2007). Specifically, a mixture of 0.5 g silicon monoxide powder and 50 mL distilled water was prepared and heated to 450 K under a pressure Of 6-10 MPa for 12 h (Lin et al., 2007).

1-3. Synthesis of Reduced Graphene Oxide Bound with Zinc Oxide Nanowires (RGO-ZnONWs)

RGO-ZnONWs were formed by dispersing RGO around ZnONWs. First, RGO powders and ZnONWs were added to distilled water. In all cases, the concentration of RGO was maintained at 1 mg/mL. The mixture was placed in an ice-water bath and subjected to sonication at a power level of 20% (BETATEK. Inc., Toronto, Canada) for 5 min.

1-4. Characterization of RGO-ZnONWs

AFM, FE-SEM, EDX, and TEM analyses were conducted on the obtained RGO-ZnONWs. For the AFM analysis, the diameters of ZnONWs and RGO-ZnONWs were measured using an In-nova microscope equipped with a nano drive controller (Bruker, Santa Barbara, Calif., USA) in air at ambient temperature and pressure. Images were recorded using a commercial cantilever tip (TESP, Veeco, USA). All images were taken with the same size of 3 μm×3 μm and a scan speed of 0.65 Hz, and recorded using the SPM Lab analysis software V7.00 (Veeco, USA). The height and two-dimensional images were obtained using the Nanoscope analysis software V1.20 (Bruker, Santa Barbara, Calif., USA). For the FE-SEM and EDX measurements, a FE-SEM (JSM-7100F, JEOL, Peabody, Mass., USA) equipped with an energy-dispersive X-ray analyzer was used at an accelerating voltage of 20 kV. TEM images were measured HRTEM (Tecnai 20, FEI, Hillsboro, Oreg., USA) was used at an accelerating voltage of 200 kV.

1-5. Fabrication of ssDNA Immobilized Microresonator

A resonator (PPP-NCH-Au, Bruker, Madison, Wis., USA) having dimensions of 30 μm×40 μm ×125 μm (width× thickness×length) and a strength of 40 N/m and surface coated with a gold film. First, the resonator was washed with distilled water and dried in a desiccator at room temperature and pressure for 1 day. After incubation, the resonator was immersed in a piranha solution ($H_2O_2$ and $H_2SO_4$ (1:2, v/v)) for 2 min, rinsed several times with distilled water, and dried in the desiccator. For ssDNA immobilization, the resonator was immersed in the tris-EDTA buffer solution with 100 μM of ssDNA for 2 h. Thereafter, the resonator was washed in distilled water and dried in the desiccator at room temperature and pressure for 1 day.

1-6. Evaluation of the Ability of ssDNA Immobilized Resonator with RGO-ZnONWs (Hereinafter Also Referred to as "Inventive Sensor" to Detect ZnONWs To evaluate the sensitivity of the inventive resonator, solutions of ZnONWs at different concentrations (1 mg/mL, 100 μg/mL, 10 μg/mL, 100 ng/mL, 1 ng/mL, and 0 mg/mL) were prepared. Then, the ssDNA immobilized resonator was immersed in each RGO-ZnONWs solution for 1 day in order to completely adsorb the RGO-ZnONWs. After immersion, the resonator was washed with DMSO. Then, the resonator was dried for 1 day in the desiccator and the resonance frequency was measured using an AFM oscillator program (Veeco, Santa Barbara, Calif., USA).

1-7. Evaluation of the Ability of the Inventive Sensor to Selectively Detect ZnONWs in Tap Water To evaluate the selective detection of zinc oxide, the detection of ZnONWs by the inventive sensor was compared with the detection of $SiO_2$NWs and AgNWs. Similarly to the preparation of the ZnONWs solutions, $SiO_2$NWs and AgNWs solutions were prepared by sonicating each nanowire type with 100 μg/mL of RGO in distilled water. After sonication, the ssDNA immobilized resonator was immersed in each solution and washed with DMSO. Then, the resonator was dried for 1 day in a desiccator and the resonance frequency was measured. The detection of ZnONWs in real tap water (Korea University, Seoul, Korea) was measured using the same procedure as described above, confirming the detection performance of the resonator in the real water system.

2. Results 2-1. Characterization of RGO-ZnONWs

Figure 2:
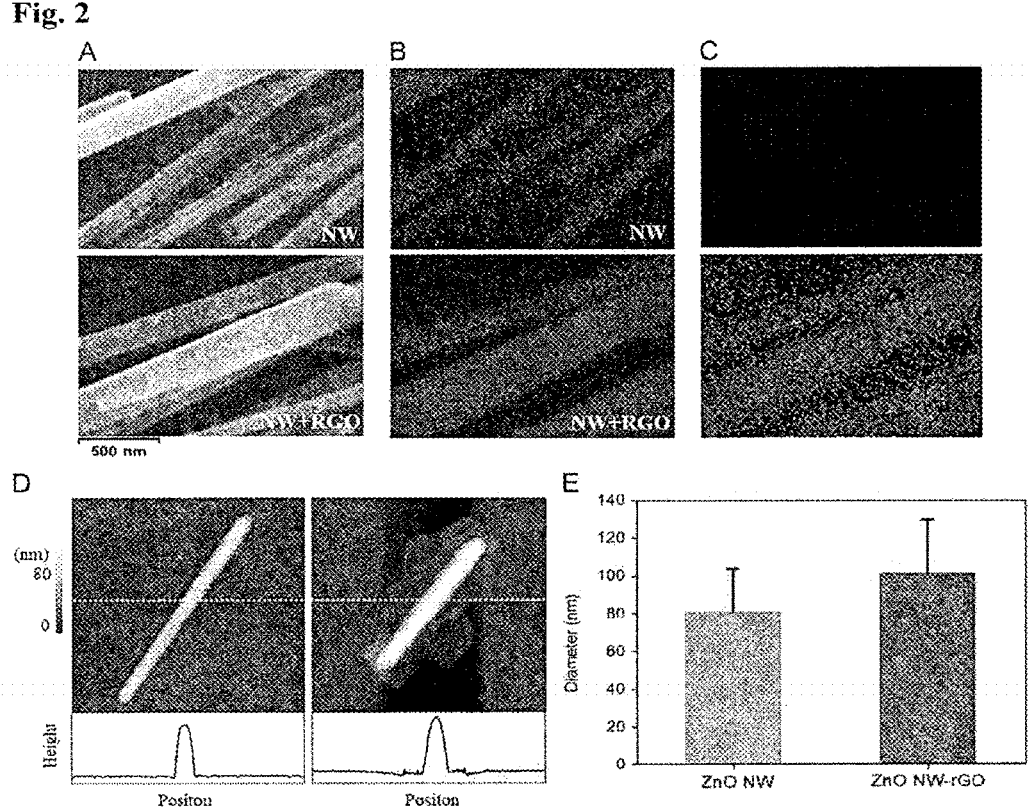
FIG. 2 compares the characteristics of reduced graphene oxide bound with zinc oxide nanowires (RGO-ZnONWs) with those of bare zinc oxide nanowires (ZnONWs): (A) scanning electron microscopy (SEM) images of RGO-ZnONWs and bare ZnONWs, (B) and (C) energy dispersive X-ray spectroscopy (EDX) images of RGO-ZnONWs and bare ZnONWs for zinc peak (B) and carbon peak (C), respectively, (D) atomic force microscopy (AFM) images of RGO-ZnONWs and bare ZnONWs, and (E) compares the diameters of RGO-ZnONWs and bare ZnONWs.
Figure 3:
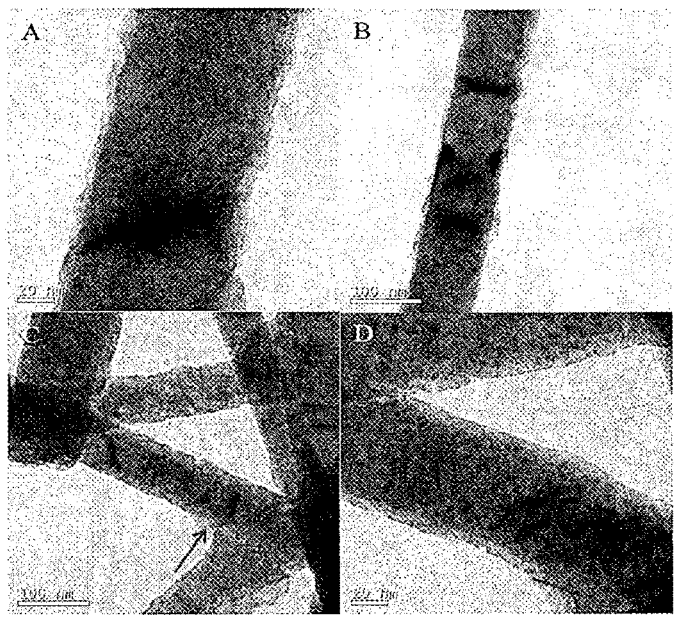
FIG. 3 shows (A) and (B) a transmission electron microscopy (TEM) image of bare ZnONWs and its higher magnification image, respectively, and (C) and (D) a TEM image of RGO-ZnONWs and its higher magnification image, respectively: The red arrow represented in (C) indicates the presence of RGO bound around ZnONWs and the red lines represented in (D) shows the thickness of RGO (~20 nm)
Figure 4:
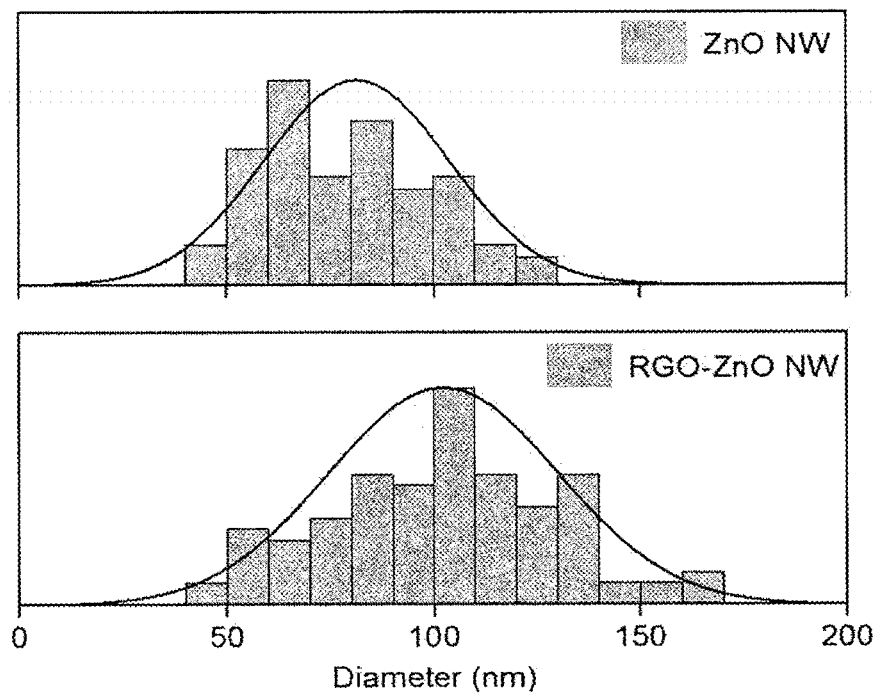
FIG. 4 shows the diameter distributions of RGO-ZnONWs and bare ZnONWs: Each diameter distribution was obtained by measuring the diameters of 100 or more samples, the average diameters of bare ZnONWs and RGO-ZnONWs were found to be 81.5±2.7 nm and 101.9±2.7 nm, respectively, and the p-test results show a significant difference in the diameter of the two groups (p-value=$2.6 \times 10^{-7}$)

The solution of RGO and ZnONWs was sonicated in distilled water to form ROG-ZnONWs in which RGO were bound with ZnONWs. In order to verify the presence of the formed RGO-ZnONWs, the SEM, EDX, and AFM images of the RGO-ZnONWs were compared with those of bare ZnONWs (FIG. 2). The SEM images show similar morphologies of ZnONWs and RGO-ZnONWs due to the presence of the same nanowires ((A) of FIG. 2). The EDX images also show similar zinc peaks along the whole length of the nanowires, as represented in the red color in (B) of FIG. 2. However, the carbon peaks were observed only on the RGO-ZnONWs, uniformly along its surface, as represented in the green color in (C) FIG. 2. The carbon peaks are the evidence of the presence of RGO on the surface, confirming that RGO is well coated on the surface of the ZnONWs. (D) of FIG. 2 shows AFM images for the structures of bare ZnONWs and RGO-ZnONWs AFM. The bare ZnONWs had a clean nanowire structure while 10 nm thick flakes were observed in RGO-ZnONWs. The formation of the flakes is attributed to an excess of RGO caused by the larger size of RGO (100 nm) compared to the circumference of the ZnONWs (80 nm). From the TEM images (FIG. 3), ZnONWs and RGO-ZnONWs were observed to have average diameters of 81.5±2.7 nm and 101.9±2.7 nm, respectively ((E) of FIG. 2 and FIG. 4). The difference in diameter corresponds to about twice the thickness of RGO. This confirms that ZnONWs were well coated with RGO.

2-2. Evaluation of the Ability of the Inventive Sensor to Detect ZnONWs

In order to evaluate the sensitivity of the inventive sensor to ZnONWs, the resonance frequency shifts of the resonator were measured with respect to varying concentrations of ZnONWs. At this time, the resonance frequency shift, $\omega_{nrfs}$, is given by:

$$\omega_{nrfs} = \delta_\omega \times 100/\omega_0$$

where $\delta_\omega$ represents the resonance frequency shift caused by zinc oxide nanowire binding and $\omega_0$ represents the resonance frequency after ssDNA immobilization.

Figure 5:
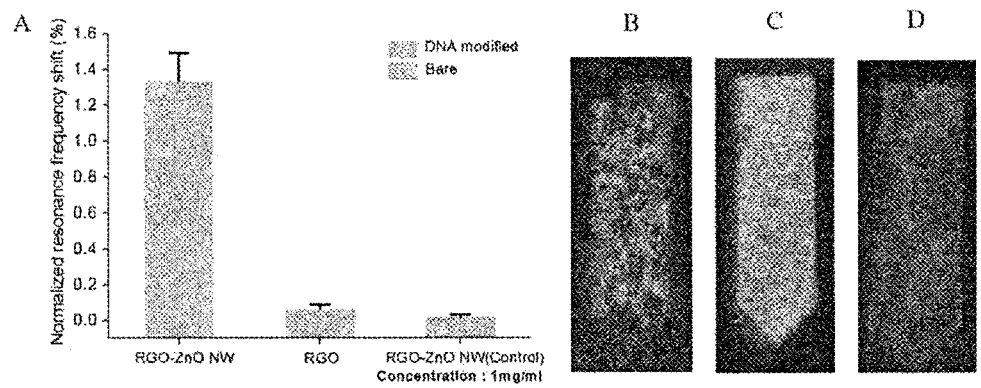
FIG. 5 shows (A) a graph comparing the resonance frequency shifts of an ssDNA immobilized resonator with RGO-ZnONWs, an ssDNA immobilized resonator with RGO, and a bare resonator (without ssDNA immobilization) with RGO-ZnONWs: Each of RGO-ZnONWs and RGO used in this experiment had a concentration of 1 mg/ml, (B) to (D) optical images of the ssDNA immobilized resonator with RGO-ZnONWs, the ssDNA immobilized resonator with RGO, and the bare resonator (without ssDNA immobilization) with RGO-ZnONWs.
Figure 6:
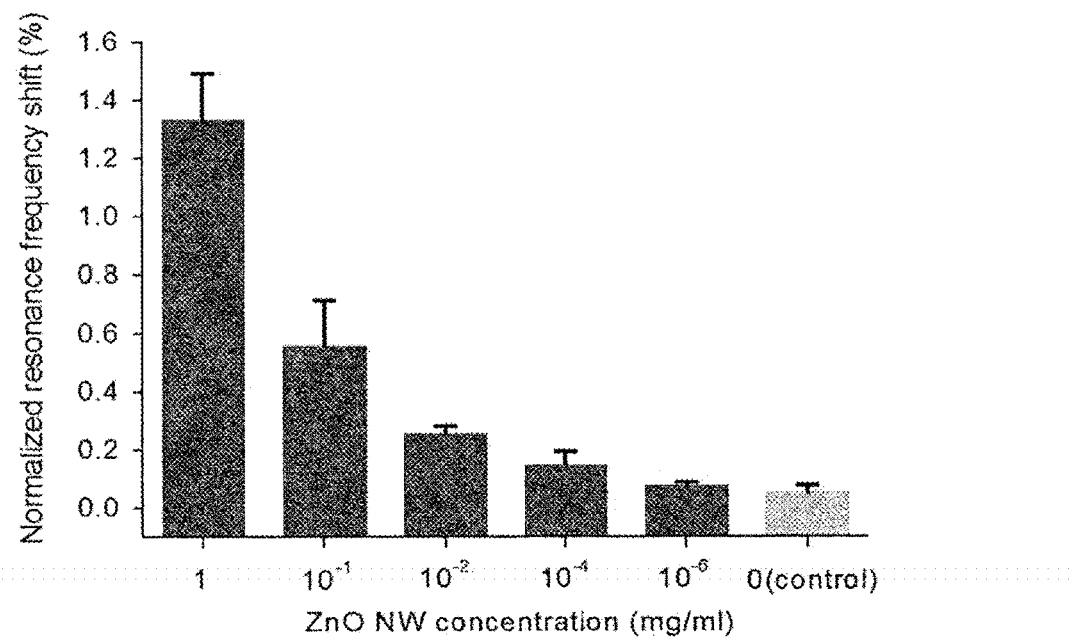
FIG. 6 is a graph showing the normalized resonance frequency shift of an ssDNA immobilized resonator with RGO-ZnONWs according to the present invention in distilled water with respect to varying concentrations of ZnONWs: The concentration of RGO was maintained to be 1 mg/ml.
Figure 7:
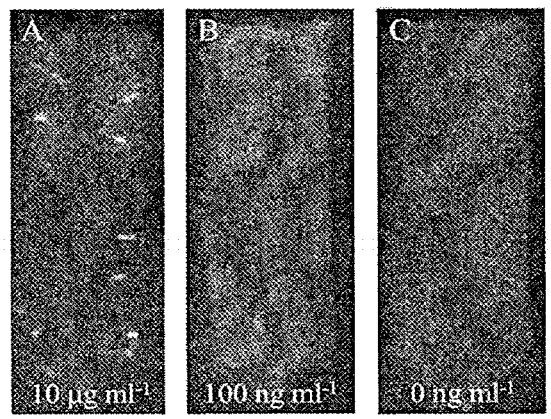
FIG. 7 shows optical images of an ssDNA immobilized resonator with RGO-ZnONWs according to the present invention at different ZnONWs concentrations of 10 μg/ml (A), 100 ng/ml (B), and 0 ng/ml (C)

(A) of FIG. 5 is a graph comparing the resonance frequency shifts of the inventive ssDNA immobilized resonator with RGO-ZnONWs, an ssDNA immobilized resonator with RGO, and a bare resonator (without ssDNA immobilization) with RGO-ZnONWs. This graph shows the resonance frequency shifts of the ssDNA immobilized resonator with the excess of RGO existing in solution and the bare resonator with RGO-ZnONWs. The resonance frequency shifts of the ssDNA immobilized resonator with RGO and the bare resonator with RGO-ZnONWs were measured to be 0.06±0.03% and 0.02±0.01%, respectively. In contrast, the resonance frequency shift of the inventive ssDNA immobilized resonator with RGO-ZnONWs was measured to be 1.34±0.16%. The larger resonance frequency shift of the ssDNA immobilized resonator with RGO-ZnONWs indicates that the larger resonance frequency shift is due to the interaction between RGO-ZnONWs and ssDNA rather than due to the interaction between RGO and ssDNA or the interaction between RGO-ZnONWs and gold on the surface of the bare resonator. Further, the resonance frequency shifts of the ssDNA immobilized resonator with RGO-ZnONWs with respect to varying concentrations of RGO-ZnONWs were measured (FIG. 6). The resonance frequency shifts for the concentrations of 1 mg/mL, 100 µg/mL, 10 µg/mL, 100 ng/mL, 1 ng/mL, and 0 g/mL (control) were found to be 1.34±0.16%, 0.56±0.15%, 0.26±0.02%, 0.15±0.03%, 0.09±0.01%, and 0.05±0.02% (control), respectively. Optical images of each resonator after detection were obtained (FIG. 7). As a result, RGO-ZnONWs were observed all over the area of the resonator and the surface coverage of the resonator increased as the concentration of RGO-ZnONWs increased. The surface coverage is directly related to the mass loading and the increased surface coverage led to the resonance frequency shift. No significant difference was observed between the RGO-ZnONWs concentration of 1 ng/ml and the control. In contrast, the resonance frequency shift measured for the RGO-ZnONWs concentration of 100 ng/mL was 3 times higher than that for the control. Thus, 100 ng/mL was considered as the limit of detection (LOD). This LOD is very meaningful because its value is about one hundredth of the observed toxicity concentration of ZnONWs (10 µg/mL) in human cells (Müller et al., 2010). This result demonstrates the ability of the inventive sensor to detect ZnONWs with very high sensitivity and early detect ZnONWs in liquid.

2-3. Selective Detection of ZnONWs Using the Inventive Sensor

Figure 8:
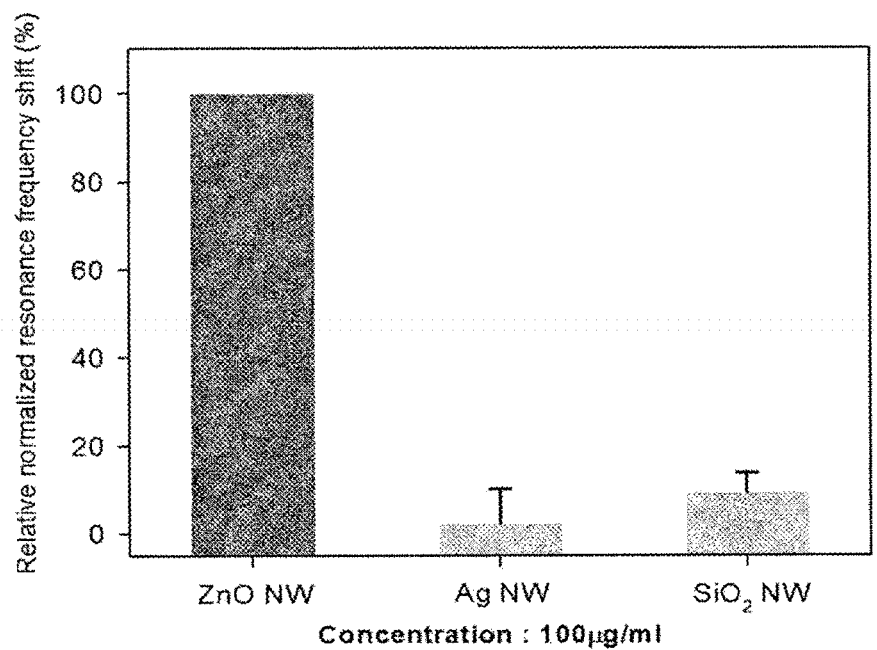
FIG. 8 is a graph confirming the selectivity of a sensor of the present invention for ZnONWs: The resonance frequency shifts of zinc oxide nanowires (ZnONWs) and silver nanowires (AgNWs) were normalized to that of the zinc oxide nanowires (ZnONWs) and the concentrations of the nanowires for the three groups were all set to 100 μg/ml and the concentration of RGO was set to 1 mg/ml.

To investigate the selectivity of the inventive sensor for ZnONWs, the sensitivities of the inventive sensor to AgNWs and SiO$_2$NWs were measured. The reason why AgNWs and SiO$_2$NWs were chosen for the comparison is their toxicity and nanowire structure. Their detections were performed at a concentration of 100 µg/mL. For the direct comparison with ZnONWs, their resonance frequency shifts were normalized to that of ZnONWs (FIG. 8). The NRFS values for AgNWs and SiO$_2$NWs were 2.5±7.7% and 9.6±4.3%, respectively, compared to that of ZnONWs (100%). Such low NRFS values of AgNWs and SiO$_2$NWs indicate very high selectivity of the inventive sensor for ZnONWs. This highly selective detection capability results from strong Van der Waals attractive forces between ZnONWs and RGO. This result demonstrates that the inventive sensor has very high selectivity for ZnONWs in real environments.

Figure 9:
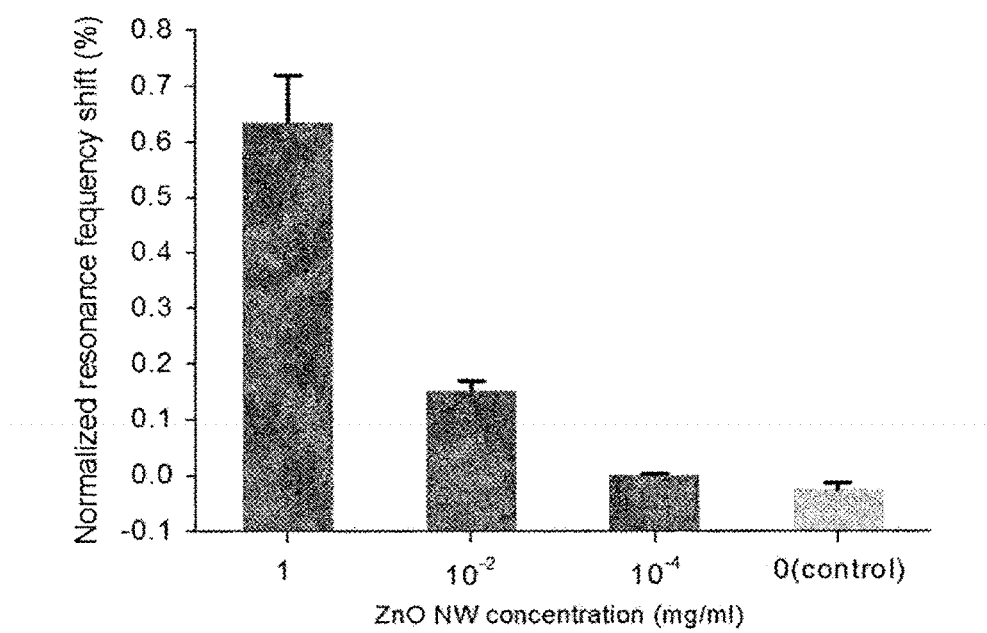
FIG. 9 is a graph showing the normalized resonance frequency shifts of an ssDNA immobilized resonator with RGO-ZnONWs according to the present invention in tap water with respect to varying concentrations of ZnONWs. The concentration of RGO was maintained to be 1 mg/ml.

2-4. Evaluation of the Ability of the Inventive Sensor to Detect ZnONWs in Tap Water In order to evaluate the ability of the inventive sensor to detect zinc oxide nanowires in a real condition, zinc oxide nanowires in real tap water were detected using the inventive sensor. The experimental procedure was the same used for the detection in distilled water, except that deionized water was replaced with real tap water. As shown in FIG. 9, the detection measurements were conducted under varying concentrations. The measured resonance frequency shift values for 1 mg/mL, 10 µg/mL, 100 ng/mL, and 0 g/mL (control) were 0.64±0.08%, 0.16±0.02%, 0.002±0.001%, and 0.02±0.01%, respectively. Similar to the detection in distilled water, the NRFS in tap water was observed to increase as the ZnONWs concentration increased. Compared to the distilled water, the NRFS values of tap water were slightly lower, which seems to be attributed to the presence of ions or impurities in tap water. Such substances are estimated to affect the ssDNA immobilized on the resonator. As a consequence, the interaction between RGO and ssDNA immobilized on the resonator was weakened. While no significant difference between the concentration of 100 ng/mL and the control (0 g/mL) was observed, the NRFS measured for the RGO-ZnONWs concentration of 10 µg/mL was significantly higher than that for the control. That is, the LOD in real tap water was measured to be 10 µg/mL. Despite the slight decrease of the NRFS in real tap water, the LOD of 10 µg/mL is almost the same as the observed toxicity concentration (10 µg/mL) of zinc oxide nanowires in human cells. Therefore, this result demonstrates the ability of the inventive sensor to detect ZnONWs in the real water system with very high sensitivity.

As discussed previously, the novel sensor and method for the detection of ZnONWs uses the self-aggregation mechanism between ZnONWs and RGO resulting from the strong Van der Waals attractive forces between the zinc atoms (Zn) of ZnONWs and the carbon atoms (C) of RGO and the strong interaction between single-stranded DNA (ssDNA) immobilized on the microresonator and RGO.

The results in the above Examples section show that the adsorption of RGO-ZnONWs onto the ssDNA immobilized resonator is much stronger than that onto the bare resonator. The LOD of the inventive sensor in distilled water was measured to be about one hundredth of the reported toxicity concentration of zinc oxide nanowires (10 µg/mL) in the human body. The LOD in real tap water was measured to be 10 µg/mL, corresponding to the concentration at which toxicity in the human body is caused. The high selectivity of the inventive sensor for ZnONWs was also confirmed, demonstrating the ability of the inventive sensor to detect ZnONWs with high selectivity and sensitivity and early detect ZnONWs in liquid. Therefore, the sensor and method of the present invention can provide powerful tools for analyzing the toxicity of ZnONWs to the environment and humans.

What is claimed is:

1. A sensor for detecting zinc oxide nanowires in water, comprising:
   a carbon material capable of binding with zinc oxide nanowires in water;
   single-stranded DNA (ssDNA) capable of selectively binding to the carbon material; and
   a microresonator,
   wherein the single-stranded DNA is immobilized on a surface of the microresonator.

2. The sensor of claim 1, wherein the carbon material is selected from the group consisting of reduced graphene oxide, graphene oxide, carbon nanotubes, and mixtures thereof.

3. The sensor of claim 1, wherein the single-stranded DNA comprises a plurality of thymine bases.

4. The sensor of claim 3, wherein the single-stranded DNA is 5'-(TTT)$_n$-3' where 1<n<20.

5. The sensor of claim 1, wherein the carbon material, the single-stranded DNA, and the microresonator are included such that a mass of the microresonator increases when the carbon material binds to the single-stranded DNA to cause a shift of resonance frequency.

6. The sensor of claim 1, wherein the single-stranded DNA has the nucleotide sequence of SEQ ID NO: 1.

7. The sensor of claim 1, wherein the carbon material is reduced graphene oxide.

8. A method for detecting zinc oxide nanowires in water, comprising:
   (a) preparing a liquid sample comprising zinc oxide nanowires and adding a carbon material capable of binding with the zinc oxide nanowires to the liquid sample such that a surface of the zinc oxide nanowires is coated with the carbon material;
   (b) immobilizing single-stranded DNA (ssDNA) capable of selectively binding to the carbon material on a surface of a microresonator;
   (c) immersing the surface of the microresonator in the liquid sample to induce selective binding between the carbon material and the single-stranded DNA; and
   (d) analyzing a resonance frequency shift of the microresonator caused by a mass increase of the microresonator due to the selective binding between the carbon material and the single-stranded DNA.

9. The method of claim 8, wherein the carbon material is selected from the group consisting of reduced graphene oxide, graphene oxide, carbon nanotubes, and mixtures thereof.

10. The method of claim 8, wherein the single-stranded DNA comprises a plurality of thymine bases.

11. The method according to of claim 10, wherein the single-stranded DNA is 5'-(TTT)$_n$-3' where 1<n<20.

12. The method of claim 8, wherein the resonance frequency shift is given by:

$$\omega_{nrfs} = \delta_\omega \times 100/\omega_0$$

where $\omega_0$ a resonance frequency measured after the immobilizing of the single-stranded DNA on the surface of the microresonator, and $\delta_\omega$ is a resonance frequency measured after the selective binding between the carbon material and the single-stranded DNA.

* * * * *